United States Patent [19]

Urban

[11] 4,259,948
[45] Apr. 7, 1981

[54] ENDOSCOPIC SYSTEM

[76] Inventor: Peter Urban, 402 Franklin, River Forest, Ill. 60305

[21] Appl. No.: 959,804

[22] Filed: Nov. 13, 1978

[51] Int. Cl.³ .......................... A61B 3/12; A61B 1/04
[52] U.S. Cl. ........................................... 128/6; 351/7; 351/16; 358/87; 358/901
[58] Field of Search ........................... 128/3–8; 128/745; 358/98, 100, 901, 87, 93; 351/7, 16; 356/241; 350/96.24–96.26

[56] References Cited

U.S. PATENT DOCUMENTS

| | | | |
|---|---|---|---|
| 3,327,712 | 6/1967 | Kaufman et al. | 358/901 X |
| 3,492,419 | 1/1970 | Bartonik | 358/87 |
| 3,542,948 | 11/1970 | Wolff | 358/87 |
| 3,655,259 | 4/1972 | Miyauchi et al. | 350/96.26 X |
| 3,821,732 | 6/1974 | Romney | 358/901 |
| 3,944,341 | 3/1976 | Pomerantzeff | 351/7 |
| 4,058,831 | 11/1977 | Smith | 358/87 |

FOREIGN PATENT DOCUMENTS 885770  7/1951  Fed. Rep. of Germany .............. 128/6

OTHER PUBLICATIONS

Ratley, "Eye-Mark Camera For Use In Driver Behavior Studies", *Med. & Biol. Engng.*, vol. 10, No. 1, pp. 101–103 (1972).
Perilhou, "Experimental Endoscope with Miniature TV camera", *Philips Tech. Rev.* 35, 166–169, 1975, No. 6.

*Primary Examiner*—Robert W. Michell
*Assistant Examiner*—Arthur S. Rose
*Attorney, Agent, or Firm*—Keil & Witherspoon

[57] ABSTRACT

An endoscopic system adapted to examine cavities, such as the inner eye includes a light source for directing at least one light beam toward the cavity to be examined to illuminate it, and a plurality of lenses for focusing the light reflected back outwardly away from the cavity along a plurality of spaced-apart paths in adjacent fields of view. A plurality of spaced-apart cameras receive the reflected light from the cavity via corresponding ones of the plurality of paths and for reproducing the adjacent fields of view.

10 Claims, 3 Drawing Figures

U.S. Patent  Apr. 7, 1981  4,259,948
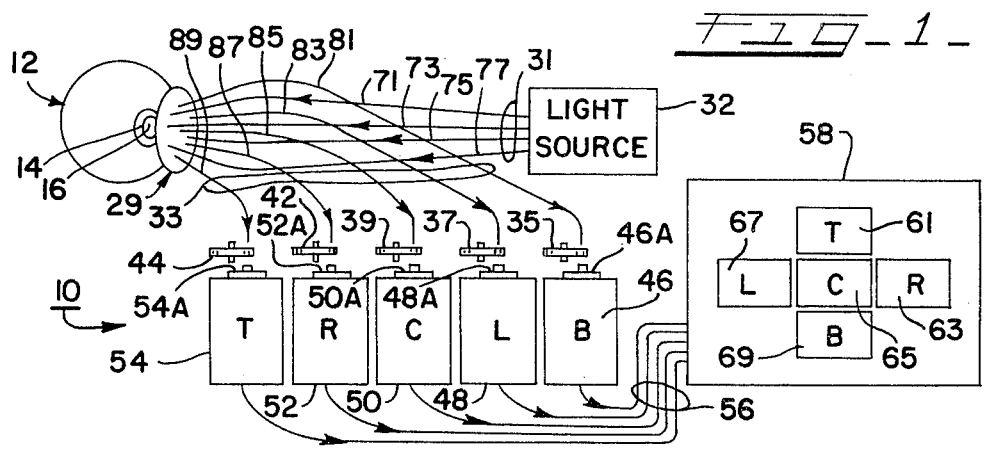
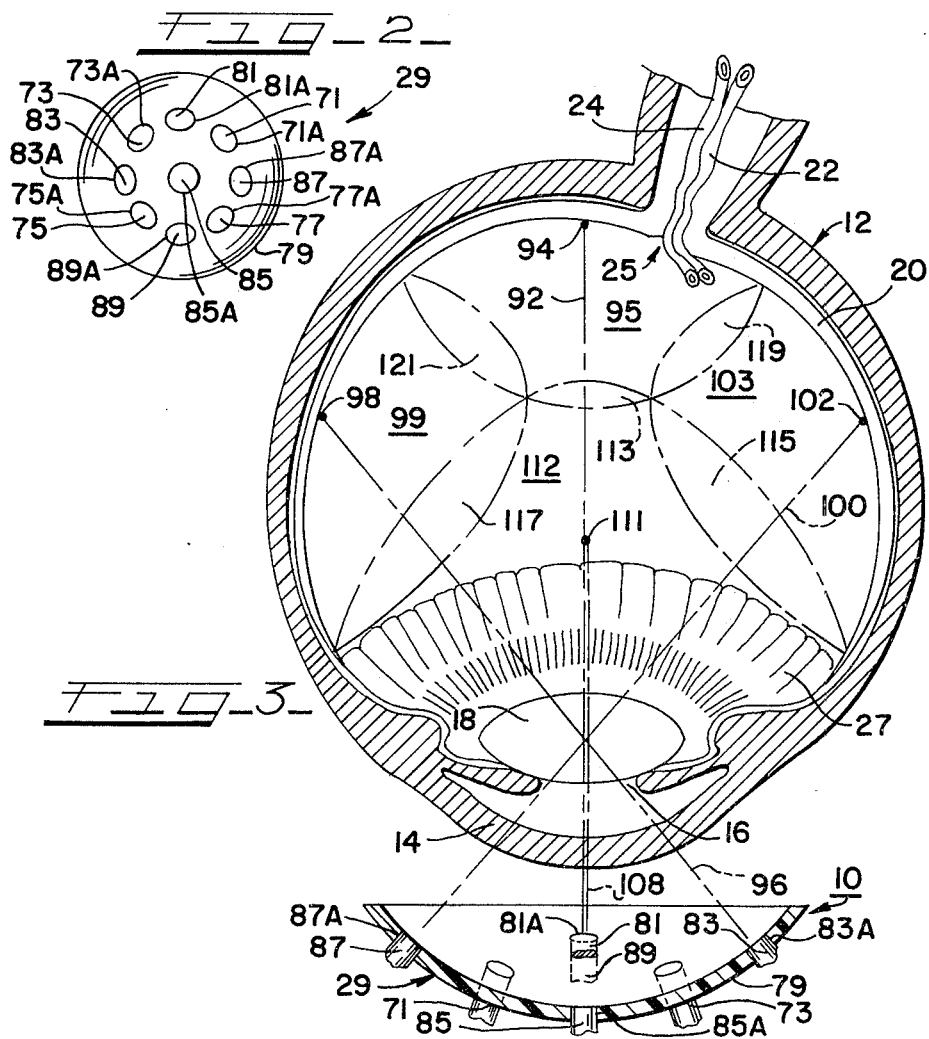

//4,259,948

ENDOSCOPIC SYSTEM

BACKGROUND OF THE INVENTION

The present invention relates in general to an endoscopic system, and it more particularly relates to an endoscopic system which is adapted to facilitate greatly the viewing of cavities in the body.

Different types and kinds of endoscopes have been used in the examination of cavities including the inner eye, the bladder, the inner ear, and the like. While the endoscopes have been satisfactory for some applications, they all suffer from various different problems all relating to the ability to facilitating the viewing of the inner surfaces of body cavities in a convenient manner. For example, in order to examine the inner eye, an ophthalmoscope is used to view the hollow spherical interior of the inner eye. Such examination is referred to as a fundus or eyegrounds examination and includes the examination of the optic disc, retina, retinal vessels, macula and the choroid. In order to perform such an examination, mydriatic solutions are used to dilate the pupil to facilitate the examination. There are basically two types of ophthalmoscopes in use today—the indirect and the direct ophthalmoscopes. The direct ophthalmoscope is a hand-held instrument which includes a strong light that can be directed into the eye under examination. The light reflected back from the fundus of the eye extends back through a small aperture in the ophthalmoscope to the examiner's eye. The aperture of the instrument is held in close proximity to the eye of the examiner as well as the eye under examination. A series of lenses usually mounted in a radially-spaced apart manner on a disc are used to focus the reflected light back to the eye of the examiner. Although such an instrument has been found to be highly successful, it enables the examiner to view the greater portion only of the retina up to the equator but not beyond the equator. It is highly desirable to view the entire retina up to the ora serrata so that ocular pathology can be detected and so that the instrument can be used conveniently during surgery. Therefore, the indirect opthalmoscope was developed and includes a convex lens which is held between the ophthalmoscope and the patient's eye under examination. The opthalmoscope includes lenses to accommodate the eye of the observer and is held several centimeters from the eye under examination. The use of the lens enables the examiner to view substantially the entire eyegrounds up to and including the ora serrata. However, the indirect ophthalmoscope provides lower magnification and produces an inverted image. It is also cumbersome to use since the ophthalmoscope, including the light source, is mounted on the head of the examiner and the lens is held in the hand. Such a device is somewhat difficult to use and requires a great deal of experience before an examining physician acquires the skill necessary to properly use it. Additionally, in both the direct and indirect ophthalmoscope, the examining physician must employ skillful hand-eye coordination to scan the eyegrounds during the examination. At all times, the examining physician must retain the fundus disc in view for orientation purposes, otherwise the physician is unable to know what portion of the eyegrounds is being visualized. Thus, the physician must acquire the necessary skill through repeated use. Additionally, during eye surgery, the use of the hand-held ophthalmoscopes requires difficult manipulations to employ the surgical instruments necessary to perform the surgical procedure as well as viewing the eyegrounds to observe the area in question. Ordinarily, the physician performing surgery on an eye views the eyegrounds through the ophthalmoscope and then uses the surgical instrument without visualizing the eyegrounds. After performing the surgical procedure, the physician sets aside the surgical instrument and then views the surgical area by means of the ophthalmoscope, and thus such a procedure is awkward and time consuming. Therefore, it would be desirable to view the eyegrounds without the necessity of holding a part or all of the ophthalmoscope in the hand so that the hands can be freed to use the surgical instruments. Also, in a teaching institution, for example, a student must attempt to view the eyegrounds for educational purposes and the teacher is unable to know exactly what the student is seeing through the ophthalmoscope, and, therefore, it would be desirable to establish an image of the cavity of the eye or other cavity of the body for several persons to view.

Therefore, while the ophthalmoscope currently being used has been satisfactory for some applications, it would be highly desirable to have a new and improved endoscopic system, which can view large areas of a cavity of the body. For example, it would be desirable to have an improved ophthalmoscopic system which can view substantially all of the retina up to the ora serrata. Such an opthalmoscopic system should be convenient to use and not require a great deal of hand-eye coordination so as to greatly eliminate or reduce the amount of time necessary in learning how to use the ophthalmoscopic system in a proper manner. Such an ophthalmoscopic system should provide the examining physician with an image of the retina without requiring the physician to hold in his hands any part of the ophthalmoscopic system so as to free his hands for other activities, such as using surgical instruments during a surgical procedure. Such a new and improved ophthalmoscopic system should also enable the physician to quickly view an image of the eyegrounds under examination and then record that image photographically for record purposes, since it is oftentimes desirable to observe any subtle changes occurring in the eyegrounds over a period of time, whereby a physician using the improved ophthalmoscopic system could examine a patient's eyes periodically and record pictures of the eyegrounds for comparison purposes to alert the physician as to any pathological changes occurring so that early treatment can be accomplished.

Therefore, in general, the principal object of the present invention is to provide a new and improved endoscopic system, which enables an examining physician to clearly visualize large areas of the interior of cavities within the body in a convenient manner with little or no need for hand-eye coordination, and which can be used to create an image of the interior of the cavity that can be conveniently photographed for record purposes.

Another object of the present invention is to provide such a new and improved endoscopic system, which can create an image of large areas of the interior of the cavity so that a single photograph can be taken of them for record purposes, and which can facilitate surgical procedures by eliminating the need for the physician to hold parts of the viewing instrument in the hand while performing the surgical procedure.

Briefly, the above and further objects of the present invention are realized by providing an endoscopic system, which includes a light source for directing at least one light beam toward the interior of the cavity under examination to illuminate it and a plurality of lenses for focusing the light reflected back outwardly away therefrom along a plurality of spaced-apart paths in adjacent fields of view. A plurality of spaced-apart camera devices receives the reflected light from the illuminated cavity via corresponding ones of the plurality of paths and reproduce the adjacent fields of view. According to the preferred form of the present invention, the camera devices include closed-circuit color television cameras which are connected electrically to a plurality of color television receivers having their video display screens positioned adjacent to one another to provide a composite image of the cavity under examination. Such image can be readily photographed by, for example, an instant still camera which can provide a photograph of the composite image in a short time for record purposes. Also, the television cameras can also be connected into a closed-circuit television system of a teaching institution or a hospital so that the composite image of the cavity can be viewed remotely for education purposes. Also, the composite image can be transmitted over telephone lines or the like to remote locations for diagnosis by specialists.

The invention, both as to its organization and method of operation, together with further objects and advantages hereof, will best be understood by reference to the following detailed description taken in connection with the accompanying sheet of drawings, wherein:

FIG. 1 is a schematic drawing of the endoscopic system, which is constructed in accordance with the present invention;

FIG. 2 is an enlarged elevational view of the input device for the system of FIG. 1; and FIG. 3 is a horizontal cross-sectional partly schematic view of a human eye under examination by the system of FIG. 1, the veins and arteries of the eye not being shown for illustration purposes.

DETAILED DESCRIPTION

Referring now to FIG. 1 of the drawings, there is shown an endoscopic system 10, which is constructed in accordance with the present invention, and which is in the form of an ophthalmoscopic system adapted to examine an eye 12. While the system 10 is shown and described to be an ophthalmoscopic system, it will become apparent to those skilled in the art that the system 10 may be used for facilitating the examination of various different cavities of the body, such cavities including the bladder, the inner ear and the like. As best seen in FIG. 3 of the drawings, the system 10 is positioned in front of a pupil 16 formed by a dilated iris 17 of the eye 12 for viewing through a lens 18 of the eye 12 its retina 20 as well as the veins (not shown) and arteries (not shown) extending from a central retinal vein 22 and a central retinal artery 24 of the optic disc 25 at the rearmost portion of the spherical retina 20 extending forwardly to the ora serrata 27.

The system 10 generally comprises a light emitting and receiving device 29, which is positioned in close proximity in front of the cornea 14 of the eye 12. In this regard, the device 29 may be mounted on a stand (not shown), and the patient places his chin on a chin rest (not shown) and his forehead or eyebrow against a frame (not shown) to position the eye 12 in proper relationship during the course of the examination. It will become apparent to those skilled in the art that similar stands (not shown) for the device 29 may also be employed during surgery when the patient is reclining for the proper positioning of the device 29 relative to the eye under examination.

A group of fiber optic strands 31 are supported at their forward ends in a spaced-apart manner by the device 29 and extend to a light source 32 to direct a plurality of beams of light from the device 29 through the pupil 16 into the inner cavity of the eye 12 for illuminating it. A group 33 of fiber optic strands are supported at the forward ones of their ends in a spaced-apart manner by the device 29 for receiving the reflected light from the retina 20 and guiding it from the rear ends thereof to a series of five lens discs 35, 37, 39, 42 and 44. Each one of the rear lens discs has a series of lenses for magnifying the light emitted from the rear ends of the group 33 of fiber optic strands and focusing them on a group of five closed-circuit color television cameras 46, 48, 50, 52 and 54. A group of cables 56 interconnect electrically the five color television cameras with a color television receiver apparatus 58 having a series of five adjacent picture tubes 61, 63, 65, 67 and 69 arranged with their faces in a closely spaced contiguous cross-shaped manner as shown in FIG. 1 of the drawings to form a composite image of the retina 20 of the eye 12, the picture tubes being controlled by individual conventional circuitry (not shown).

In use, the device 29 is positioned immediately in front of and in a closely-spaced manner relative to the cornea 14 of the eye 12, the pupil 16 having been previously dilated for examination purposes. The light source 32 is then illuminated to direct light via the fiber optic strands 31 and from the forward ends thereof at the device 29 and from there through the dilated pupil 16 and into the inner cavity of the eye 12 for illuminating its retina 20. Light reflected back from the retina 20 is directed to the forward entrance ends of the group 33 of fiber optic strands and is guided by them individually from their exit ends to the lens discs. The light emitted from the group 33 of fiber optic strands is magnified by the small lenses of the lense disc to focus the light on the lens systems 46A, 48A, 50A, 52A, and 54A of the corresponding closed-circuit color television cameras 46, 48, 50, 52 and 54. The picture tubes respond to their television receiver circuits (not shown) which in turn respond individually to the outputs from the cameras to reproduce electrically a composite image of substantially all of the retina 20 extending to the ora serrata 27. In this regard, electrical signals are transmitted from the five television cameras via the group of cables 56 to the television receiver apparatus 58 to reproduce visually the five composite images via the five television picture tubes 61, 63, 65, 67 and 69.

In order to focus the five portions of the composite image, the lens discs are rotated individually to properly focus the portions of the images of the retina onto the individual lens systems of the five cameras. Once the composite image is properly in focus, the examining physician can then visualize substantially all of the retina 20 and can take a photograph with a still camera (not shown) of the faces of the picture tubes of the television receiver apparatus 58 for record purposes, or video tape record a surgical procedure.

The group 31 of fiber optic strands comprise four fiber optic strands 71, 73, 75 and 77 which extend between the light source 32 and a dish-shaped support member 79 of the device 29. As best seen in FIG. 2 of the drawings, the exit ends of the strands extend through a series of spaced-apart circular holes 71A, 73A, 75A, and 77A, respectively, arranged in a circle and are disposed flush with the forward concave face of the support member 79. The group 31 of fibre optic strands are fixed within their holes by any suitable technique, such as applying a suitable adhesive, force fit or the like. The support member 79 positions the exit ends of the group 31 of strands in a spaced-apart manner and directs the light emitted therefrom in a uniformly distributed manner for better illumination of the cavity of the eye.

The group 33 of fiber optic strands comprise five fiber optic strands 81, 83, 85, 87 and 89 which have their entrance ends fixed within and extending through a series of circular holes 81A, 83A, 85A and 87A respectively disposed within the dish-shaped support member 79 as best seen in FIG. 2 of the drawings for properly positioning them relative to the eye 12 in a manner similar to the group 31 of strands. In this regard, the exit end of the strand 81 is positioned in a flush manner on the concave front face of the member 79 near the top thereof, and the exit ends of the strands 83 and 87 are disposed at the left and right, respectively, of the front concave face of the member 79 when viewing the member from the front thereof as shown in FIG. 2, and are mounted in place in a similar manner as the end of the strand 81. The exit end of the strand 85 is similarly mounted and is positioned at the geometric center of the member 79. The exit end of the strand 89 is also similarly mounted and is disposed directly below the exit end of the strand 85. Due to the dish shape of the member 79, the reflected light from the retina 20 is picked up from different aspects of the retina 20.

Due to the flexibility of the fibre optic strands, the exit ends of the strands of the group 33 are positioned opposite the lens disc which can be sufficiently spaced apart to conveniently accommodate the television cameras and have them sufficiently remote from the patient and yet enable the examining physician or someone else in attendance to operate the lens disc for focusing purposes. Also, by employing the group 33 of fibre optic strands, a plurality of closely spaced conduits for the reflected light are provided to guide the reflected light away from the cavity under inspection to a convenient remote location.

Thus, substantially all of the retina is viewed and is reproduced in a composite of five different images by the five video picture tubes. As hereinafter described in greater detail, the five images are each overlapping with its adjacent image to provide continuity between the images. The center picture tube 65 visualizes the optic disc 25 for reference purposes, and the other four picture tubes visualize the contiguous areas so that the orientation of the observer is obviated. There is no need to continuously visualize the optic disc for orientation purposes as is the practice with the prior known ophthalmoscopes, since the central picture tube 65 displays an image of the optic disc 25 and the other picture tubes display contiguous areas so that, for example, the observer can visualize conveniently the veins (not shown) and arteries (not shown) starting at the image of the disc 25 displayed by the center tube 65 and following them to the image in a contiguous picture tube. Since the images are overlapping, the observer can readily see where the vein or artery of interest is repeated in the adjacent image.

It should be noted that since the interior of the cavity of the eye is a contoured surface and not a flat surface, as is well known in the art, the camera lens systems and the lens discs are arranged to minimize distortion when the images are reproduced on the substantially flat picture tubes.

Referring now to FIG. 3 of the drawings, the relative positioning of the fiber optic strands will be considered. The central light receiving fiber optic strand 85 of the group 33 has its entrance end 85A positioned with its axis 92 directed toward a point 94 for a field of view 95 at the central portion of the fundus of the retina. The entrance end 83A of the fiber optic strand 83 has its axis 96 extending to a point 98 at the center of a field of view 99 at the left-hand portion (temple) of the retina. The entrance end 87A of the strand 87 has its axis 100 directed to a point 102 of a field of view 103 at the right-hand portion (nasal portion) of the retina. It should be noted that the entrance end 87A of the strand 87 is disposed at the left side of the member 79 and the entrance end 83A of the strand 83 is disposed at the right side of the member 79 so that the two axes 96 and 100 cross one another and extend through the pupil 16 and the lens 18.

The entrance end 81A of the upper strand 81 is aligned along a downwardly sloping axis 108 to a point 111 within a field of view 112 at the lower portion of the retina. Similarly, the exit end 89A of the lower strand 89 is directed along an upwardly inclined axis (not shown) to a point (not shown) at the upper portion (not shown) of the retina.

As a result, the five light receiving strands receive light from five overlapping fields of view. In this regard, the central field of view 95 overlaps at 113 with the lower field of view 112. The lower field of view 112 overlaps at 115 with the right field of view 103. At the overlapping area 117, the lower field of view 112 overlaps with the left field of view 99. The central field of view overlaps at 119 with the right field of view 103. Similarly, at 121, the central field of view 95 overlaps with the left field of view 99. The upper field of view (not shown) similarly overlaps with the contiguous fields of view in a similar manner as the lower field 112 overlaps with the central, left and right fields of view.

It should be noted that it is preferred to have a field of view overlap with its contiguous fields only. For example, the overlapping area 113 between the fields 95 and 112 does not overlap with either the fields 99 or 103. In this manner, the focusing of the lens system is greatly simplified.

At the overlapping areas, a binocular effect is achieved, and thus a three-dimensional aspect image is realized by the viewer.

It should also be noted that a greater number of fiber optic strands for receiving the reflective light may be employed together with a corresponding increase in the number of cameras and picture tubes to provide an even greater resolution of the composite image.

What is claimed is:

1. An endoscopic system adapted to examine a cavity of the body and, in particular, the surface of the inner eye, said system comprising:
   means for illuminating the inner eye surface;
   a support member having a concave front face adapted to be directed toward the eye;
   a plurality of lenses mounted on said face in spaced-apart relationship with their optical axes aligned to intersect within the eye in a manner such that when said concave face is directed towards the surface of the inner eye said lenses receive multiple distinct and partially overlapping images of adjacent portions of the inner surface of the eye;

a light conducting means associated at one of its ends with said plurality of lenses for transmitting said multiple images; and a camera means for receiving said multiple images transmitted from the other end of said light conducting means and for displaying said multiple images.

2. In an endoscopic system according to claim 1, wherein said camera means includes a plurality of cameras, each of said cameras having a lens system for receiving and focusing said transmitted images.

3. In an endoscopic system according to claim 2, wherein each of said cameras includes a color television camera.

4. In an endoscopic system according to claim 3, wherein said camera means further includes color television receiver means having a plurality of video display units arranged in a side-by-side manner.

5. In an endoscopic system according to claim 4, wherein said plurality of camera means includes five television cameras and said television receiver means includes five corresponding television picture tubes for responding to said television cameras for displaying said overlapping images of adjacent portions of the inner surface of the eye.

6. In an endoscopic system according to claim 1, wherein said means for illuminating includes a light emitting means for guiding at least one light beam from a light source toward the surface of the inner eye and said means for conducting light includes a light receiving means for guiding the reflected light from said lenses to said camera means.

7. In an endoscopic system according to claim 6, wherein said light emitting and receiving means comprise fiber optic strands.

8. In an endoscopic system according to claim 7, wherein said plurality of lenses are individually associated with the ends of said light-receiving fiber optic strands, and said light-emitting fiber optic strands have one of their ends positioned on the concave front face of said support member in a spaced-apart manner and the other of their ends positioned at said light source, said endoscopic system being an ophthalmoscope.

9. The method of using the apparatus of claim 1, comprising:

directing the illuminating means toward the surface of the inner eye, and focusing said lenses by adjusting the position of the concave front face of said support member with respect to the inner surface of the eye.

10. The method according to claim 9, further including displaying said multiple overlapping images of adjacent portions of the inner surface of the eye with said camera means.

* * * * *